United States Patent
Lei et al.

(10) Patent No.: US 9,734,630 B2
(45) Date of Patent: Aug. 15, 2017

(54) REAL-TIME THREE-DIMENSIONAL VISUALIZATION OF INTERVENTIONAL MEDICAL DEVICES

(71) Applicant: Siemens Medical Solutions USA, Inc., Malvern, PA (US)

(72) Inventors: Weng Lei, Mount Prospect, IL (US); Soroosh Kargar, Lake in the Hills, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 424 days.

(21) Appl. No.: 14/569,997

(22) Filed: Dec. 15, 2014

(65) Prior Publication Data
US 2016/0171747 A1    Jun. 16, 2016

(51) Int. Cl.
| | |
|---|---|
| G06T 15/08 | (2011.01) |
| G06K 9/62 | (2006.01) |
| G06K 9/46 | (2006.01) |
| G06T 15/20 | (2011.01) |
| A61B 19/00 | (2006.01) |
| G06T 7/00 | (2017.01) |
| G06T 19/00 | (2011.01) |
| A61B 6/02 | (2006.01) |
| A61B 6/12 | (2006.01) |
| A61B 6/00 | (2006.01) |
| G06T 11/00 | (2006.01) |

(52) U.S. Cl.
CPC .............. *G06T 19/00* (2013.01); *A61B 6/022* (2013.01); *A61B 6/12* (2013.01); *A61B 6/4441* (2013.01); *A61B 6/466* (2013.01); *A61B 6/469* (2013.01); *A61B 6/505* (2013.01); *G06T 11/008* (2013.01); *A61B 2576/00* (2013.01); *G06T 2210/41* (2013.01); *G06T 2211/428* (2013.01)

(58) Field of Classification Search
CPC ....... A61B 2576/00; A61B 6/022; A61B 6/12; A61B 6/4441; A61B 6/466; A61B 6/469; A61B 6/505; G06T 11/008; G06T 19/00; G06T 2210/41; G06T 2211/428
See application file for complete search history.

(56) References Cited

U.S. PATENT DOCUMENTS

| | | |
|---|---|---|
| 7,761,135 B2 | 7/2010 | Pfister et al. |
| 2013/0172732 A1 | 7/2013 | Kiraly et al. |

*Primary Examiner* — Michael Rozanski

(57) ABSTRACT

A system and method includes acquisition of a first at least two two-dimensional images of a body, generation of a first three-dimensional image based on the first at least two two-dimensional images, acquisition of a second at least two two-dimensional images of the body, generation of a second three-dimensional image based on the second at least two two-dimensional images, determination of a difference between the first three-dimensional image and the second three-dimensional image, determination of a region of interest based on the difference, replacement of first voxels of the region of interest of the first three-dimensional image with second voxels of the region of interest of the second three-dimensional image to generate a first updated three-dimensional image, and display of the first updated three-dimensional image.

18 Claims, 9 Drawing Sheets

US 9,734,630 B2

REAL-TIME THREE-DIMENSIONAL VISUALIZATION OF INTERVENTIONAL MEDICAL DEVICES

BACKGROUND

Field

The embodiments described below relate to three-dimensional imaging of interventional medical devices.

Description

Many medical procedures include insertion of a device (e.g., needle, catheter, stent, etc.) into a patient's body. During the insertion, an imaging system acquires and displays successive two-dimensional images of the portion of the body in which the device is located. The two-dimensional images are acquired and displayed in substantially real-time, thereby providing visual feedback to an operator controlling the insertion.

The success of the procedure depends upon the three-dimensional position of the device within the body. Accordingly, the two-dimensional images are of limited assistance to the operator. Unfortunately, generation of real-time three-dimensional images having sufficient resolution is beyond the processing capability of medical imaging systems used in such procedures.

Conventional systems attempt to address the foregoing by initially generating and displaying a single three-dimensional image of the relevant portion of the patient. During a procedure, successive two-dimensional images of the portion are acquired and overlaid on the static three-dimensional image. The overlay requires registration between the two-dimensional and three-dimensional images, which introduces inaccuracies. Moreover, even if registration were accurate, the resulting composite image is distracting and not suitably representative of the three-dimensional position of the device.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments and sets forth the best mode contemplated for carrying out the described embodiments. Various modifications, however, will remain readily apparent to those in the art.

Generally, and according to some embodiments, at least two two-dimensional images of a patient are obtained. The images are obtained substantially contemporaneously and are used to generate a first three-dimensional image. A device is then inserted into the patient and a second at least two two-dimensional images are obtained. A second three-dimensional image is generated based on the second two-dimensional images.

A change is detected between the first three-dimensional image and the second three-dimensional image, and a region of interest is identified based on the detected change. For example, a portion of the second three-dimensional image may be determined to include voxels representing the inserted device, while a corresponding portion of the first three-dimensional image does not include these voxels. A region of interest which surrounds these voxels is then identified.

Voxels within the region of interest of the first three-dimensional image are replaced with voxels within the region of interest of the second three-dimensional image, and the updated first three-dimensional image is displayed. As the procedure continues, another at least two two-dimensional images are obtained. A third three-dimensional image is generated based on these two-dimensional images, but this third three-dimensional image is primarily (or exclusively) intended to represent the region of interest. Voxels within the region of interest of the first three-dimensional image are then replaced with voxels within the region of interest of the third three-dimensional image. The newly-changed first three-dimensional image is displayed.

In effect, the operator views substantially real-time three-dimensional images including the device during the procedure. However, since some embodiments only require generation of a suitable three-dimensional image of the region of interest, computational requirements are reduced in comparison to systems which attempt to generate the displayed three-dimensional image in its entirety in real-time.

Figure 1:
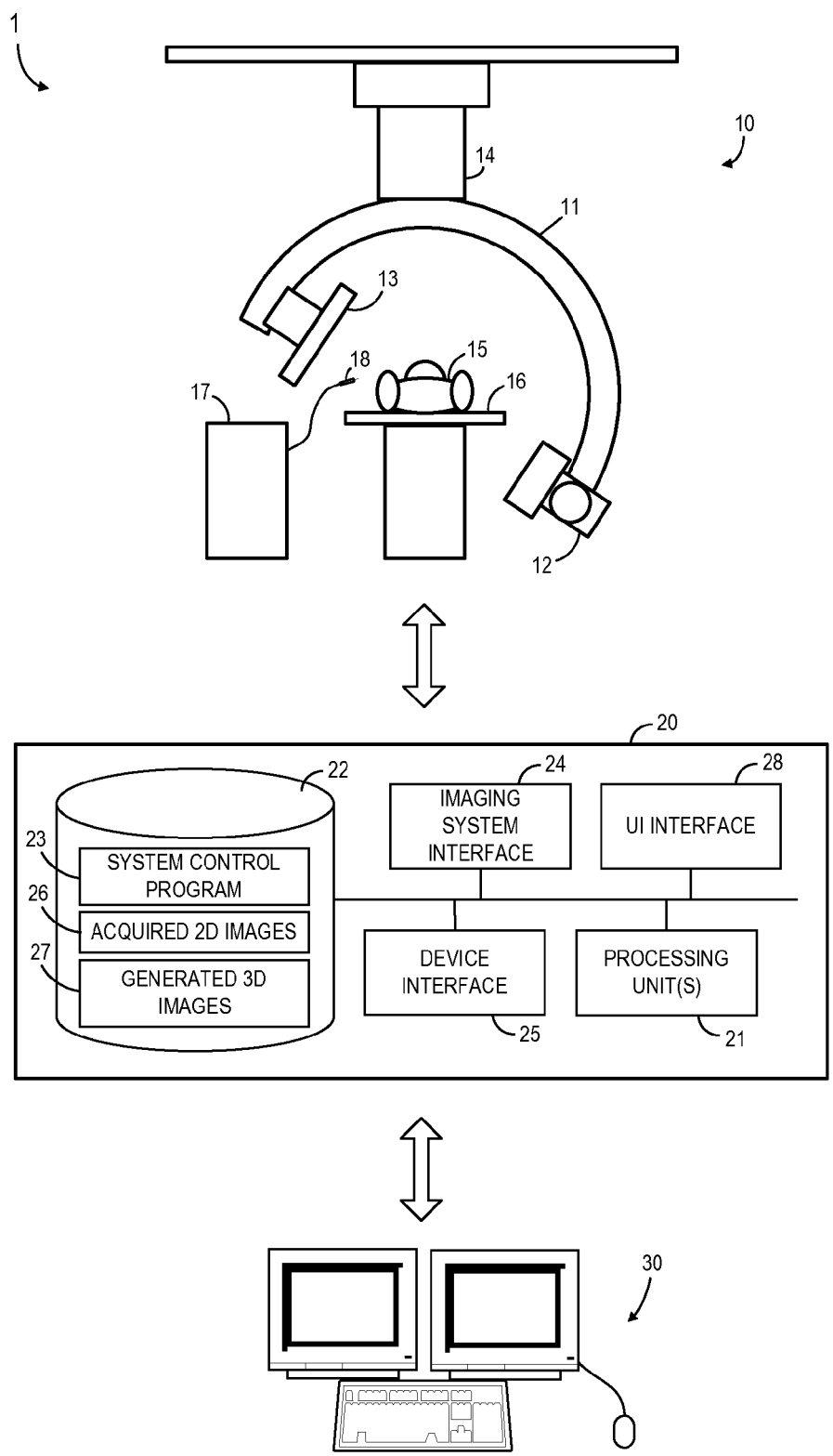
FIG. 1 illustrates a system according to some embodiments.

FIG. 1 illustrates system 1 according to some embodiments. Embodiments are not limited to the elements and/or arrangement of system 1. System 1 includes interventional system 10, control and processing system 20, and operator terminal 30. Generally, and according to some embodiments, interventional system 10 supports insertion of a device into a patent and imaging thereof. Control and processing system 20 controls imaging system 10 and receives the acquired images therefrom. Control and processing system 20 processes the images as described below and provides output to terminal 30 for display thereby. Such processing may be based on user input received by terminal 30 and provided to control and processing system 20 by terminal 30.

Interventional system 10 acquires two-dimensional images including one or more data values for each pixel of an image. These images may be acquired at different angles and used to generate a corresponding three-dimensional image using known reconstruction methods.

According to the illustrated embodiment, interventional system 10 comprises C-arm 11 on which X-ray radiation source 12 and radiation detector 13 are mounted. C-arm 11 is mounted on support 14 and is configured to translate clockwise or counter-clockwise with respect to support 14. This translation rotates radiation source 12 and radiation detector 13 around a central volume, such as patient 15 positioned on table 16, while maintaining the physical relationship there between.

Embodiments are not limited to C-arm-based systems. Interventional system 10 may comprise any system for acquiring images that is or becomes known, including but not limited to those described below with respect to FIGS. 17 and 18. According to some embodiments, interventional system 10 may comprise an x-ray imaging system, a camera, a magnetic resonance imaging system, a positron emission tomography scanner, or a computed tomography imaging system.

Radiation source 12 may comprise any suitable radiation source, including but not limited to an X-ray tube. In some embodiments, radiation source 12 emits electron, photon or other type of radiation having energies ranging from 50 to 150 keV.

Radiation detector 13 may comprise any system to acquire an image based on received x-ray radiation. In some embodiments, radiation detector 13 is a flat-panel imaging device using a scintillator layer and solid-state amorphous silicon photodiodes deployed in a two-dimensional array. The scintillator layer receives photons and generates light in proportion to the intensity of the received photons. The array of photodiodes receives the light and records the intensity of received light as stored electrical charge.

In some embodiments, radiation detector 13 converts received photons to electrical charge without requiring a scintillator layer. The photons are absorbed directly by an array of amorphous selenium photoconductors. The photoconductors convert the photons directly to stored electrical charge. Radiation detector 13 may comprise a CCD or tube-based camera, including a light-proof housing within which are disposed a scintillator, a mirror, and a camera.

The charge developed and stored by radiation detector 13 represents radiation intensities at each location of a radiation field produced by x-rays emitted from radiation source 12. The radiation intensity at a particular location of the radiation field represents the attenuative properties of tissues of patient 15 lying along a divergent line between radiation source 12 and the particular location of the radiation field. The set of radiation intensities acquired by radiation detector 13 may therefore represent a two-dimensional projection image of these tissues.

Device console 17 may comprise any suitable system to support insertable/injectable medical device 18. Insertion/injection of device 18 may be controlled by a physician or other qualified operator. Device 18 may comprise a needle (solid or hollow for delivering an injectable), a catheter, a stent, an orthopedic implant, a screw, a tool (e.g., a driver for a bone screw), or any other device that is or becomes known. In some embodiments, device 18 is not transparent to the imaging modality used by system 10.

System 20 may comprise any general-purpose or dedicated computing system. Accordingly, system 20 includes one or more processors 21 configured to execute processor-executable program code to cause system 20 to operate as described herein, and storage device 22 for storing the program code. Storage device 22 may comprise one or more fixed disks, solid-state random access memory, and/or removable media (e.g., a thumb drive) mounted in a corresponding interface (e.g., a USB port).

Storage device 22 stores program code of system control program 23. One or more processing units 21 may execute system control program 23 to move C-arm 14, to cause radiation source 12 to emit radiation, and to control detector 13 to acquire an image. In this regard, system 20 includes imaging system interface 24 and device interface 25 for communication with system 10. According to some embodiments, interface 24 supports Advanced X.25 Connection Services (AXCS) messages and interface 25 comprises an examination control console and joystick.

Images acquired from system 10 are stored in data storage device 22 as acquired images 26, in DICOM or another data format. Each acquired image 26 may be further associated with details of its acquisition, including but not limited to imaging plane position and angle, imaging position, radiation source-to-detector distance, patient anatomy imaged, patient position, x-ray tube voltage, image resolution and radiation dosage.

Processing unit(s) 21 may further execute system control program 23 to generate three-dimensional images 27 based on two or more of two-dimensional images 26, to identify regions of interest based on three-dimensional images 27 and change voxels of three-dimensional images 27 as described herein.

UI interface 28 may receive input from terminal 30, which may be used to control the acquisition of images and/or identification of the region of interest. Terminal 30 of system 1 includes two display monitors, but embodiments are not limited thereto. In some embodiments, one of the display monitors displays a three-dimensional image as described herein and the other display monitor displays a corresponding two-dimensional image.

Terminal 30 may simply comprise a display device and an input device coupled to system 20. In some embodiments, terminal 30 is a separate computing device such as, but not limited to, a desktop computer, a laptop computer, a tablet computer, and a smartphone.

Each of system 10, system 20 and terminal 30 may include other elements which are necessary for the operation thereof, as well as additional elements for providing functions other than those described herein.

According to the illustrated embodiment, system 20 controls the elements of system 10. System 20 also processes images received from system 10. Embodiments are not limited to a single system performing each of these functions. For example, system 10 may be controlled by a dedicated control system, with the acquired images being provided to a separate image processing system over a computer network or via a physical storage medium (e.g., a DVD).

Figure 2A:
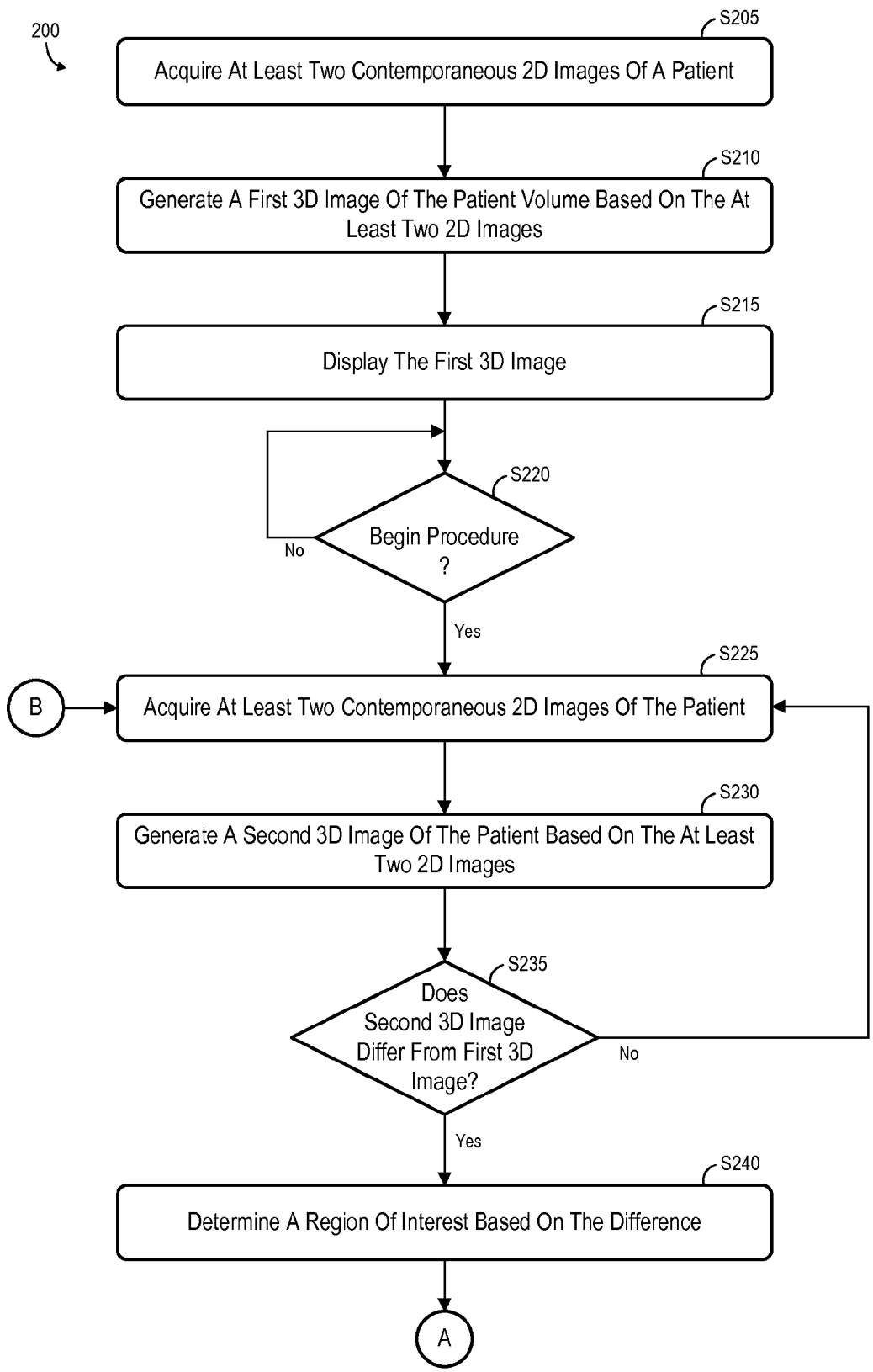
FIGS. 2a and 2b comprise a flow diagram of a process according to some embodiments.
Figure 2B:
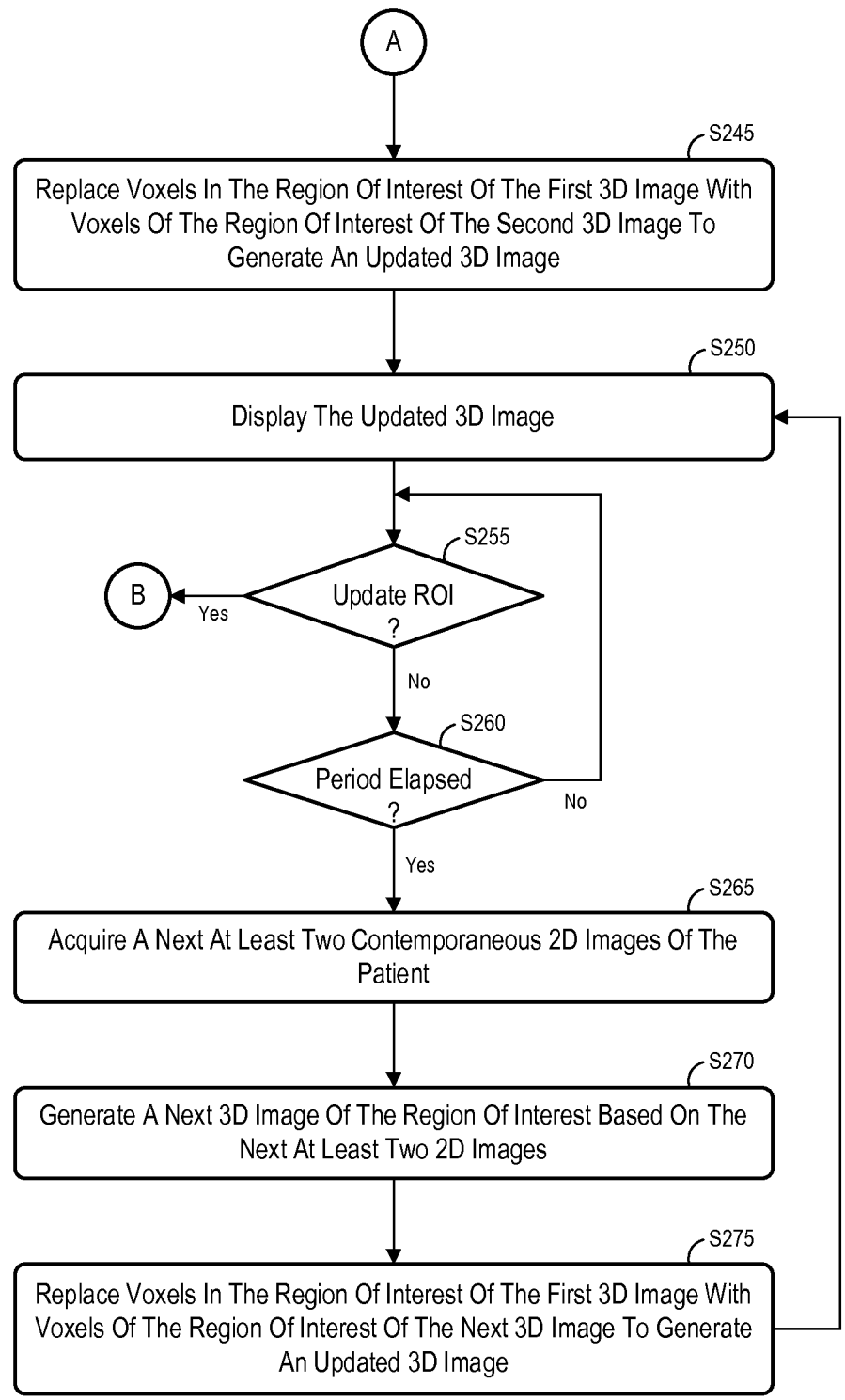

FIGS. 2A and 2B comprise a flow diagram of process 200 according to some embodiments. Process 200 and the other processes described herein may be performed using any suitable combination of hardware, software or manual means. Software embodying these processes may be stored by any non-transitory tangible medium, including a fixed disk, a floppy disk, a CD, a DVD, a Flash drive, or a magnetic tape. According to some embodiments, most or all of the steps of process 200 are embodied within executable code of system control program 23 and executed by processing unit(s) 21 of device 20.

Initially, at S205, at least two two-dimensional images of a patient are obtained. The images may be obtained within a small timeframe so that they each represent a state of the patient within the timeframe. With reference to FIG. 1, radiation source 12 and detector 13 may operate to acquire a first two-dimensional image while in a first position. Next, c-arm 11 translates with respect to support 14 so that source 12 and detector 13 are in different positions relative to patient 15, and a second two-dimensional image is acquired. Any number of two-dimensional images may be acquired at S205. As will be described below, some systems acquire two or more of the two or more images of S205 substantially simultaneously. According to some embodiments, at least two of the images acquired at S205 are acquired at least 30 degrees apart from one another.

A first three-dimensional image is generated at S210 based on the images acquired at S205. The first three-dimensional image may be generated using any technique that is or becomes known, including but not limited to back-projection, LaPlace, and/or other reconstruction techniques. The first three-dimensional image may be generated using parameters which provide a reasonably clear three-dimensional image throughout the entire volume of the three-dimensional image.

Figure 3:
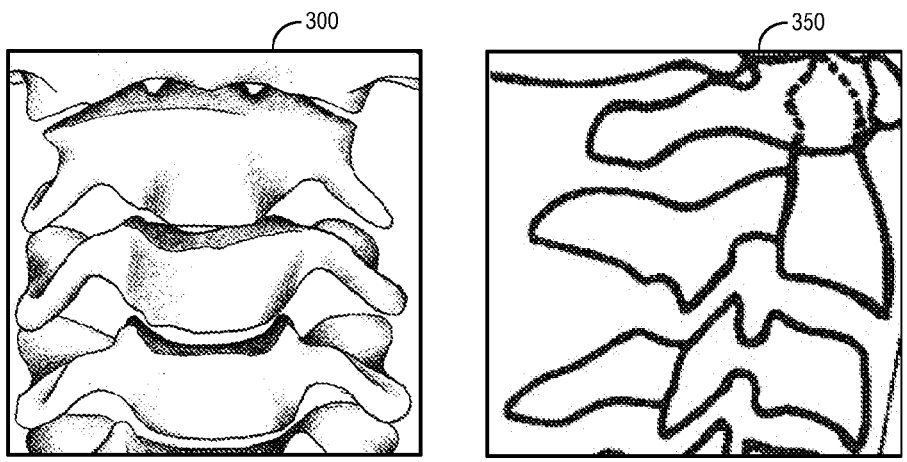
FIG. 3 comprises views of a three-dimensional image of a portion of a body and a corresponding two-dimensional image of the portion of the body.

The first three-dimensional image is displayed at S215. According to some embodiments, the first three-dimensional image is displayed on one of the two display monitors of terminal 30, and one of the two-dimensional images acquired at S205 is displayed on the second display monitor. The foregoing arrangement may provide an operator with a comfortable degree of confidence during a subsequent interventional procedure. FIG. 3 illustrates such an arrangement, including three-dimensional image 300 and two-dimensional image 350.

Flow cycles at S220 while waiting for the interventional procedure to begin. That is, according to the present example, no further images are acquired or displayed until the procedure begins. Flow proceeds to S225 once the procedure begins. For example, the operator may operate a displayed user interface, or initiate operation of device control 17, to indicate that the procedure has begun at S220.

Next, according to some embodiments, an interventional device is inserted into the patient and a second at least two two-dimensional images are acquired at S225. The second at least two two-dimensional images may be acquired at S225 in a same or different manner than the acquisition at S205. The number of images acquired at S225 may be the same or different than the number acquired at S205. A second three-dimensional image is generated at S230 based on the second two-dimensional images.

At S235, it is determined whether the three-dimensional image generated at S230 differs from the three-dimensional image generated at S210. Any image comparison algorithm that is or becomes known may be used in some embodiments of S235. The determination at S235 may be associated with a threshold amount. That is, if the difference between the two images is less than the (non-zero) threshold amount, the determination of S235 is negative and flow returns to S225 as pictured. On the other hand, the determination is affirmative and flow proceeds to S240 if the difference (as quantified by the particular algorithm used) is greater than the threshold amount.

The aforementioned threshold amount may be calibrated to facilitate detection of an interventional device within the second three-dimensional image. That is, the threshold amount may be set at a level which results in an affirmative determination at S235 in a case that an interventional device is pictured within the second three-dimensional image. Accordingly, the threshold may be set based on a size of a particular device to be used during the current procedure.

As mentioned above, flow returns to S225 if the determination of S235 is negative. Accordingly, flow cycles between S225, S230 and S235 until it is determined at S235 that the second three-dimensional image is sufficiently different from the first three-dimensional image.

Figure 4:
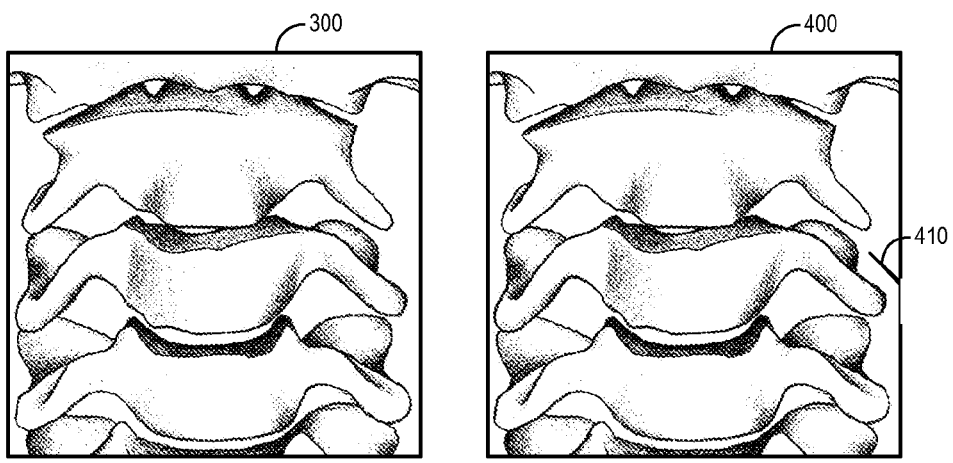
FIG. 4 comprises views of a three-dimensional image of a portion of a body and a later-obtained three-dimensional image of the portion of the body.

FIG. 4 illustrates first three-dimensional image 300 and second three-dimensional image 400 for purposes of describing the present example; both of these images are most likely not simultaneously presented to the operator. Second three-dimensional image 400 depicts interventional device (e.g., a needle) which has been inserted into the patient at some time during cycling of flow between S225, S230 and S235. It will be assumed that the difference between image 300 and image 400 is deemed to be sufficient to result in an affirmative determination at S235.

Figure 5:
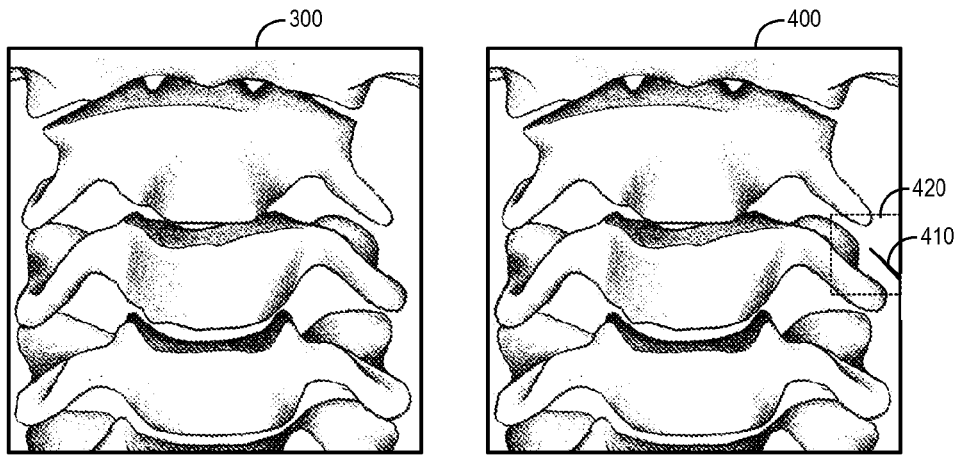
FIG. 5 comprises views of a three-dimensional image of a portion of a body and a later-obtained three-dimensional image of the portion of the body illustrating detection of a changed region.

Flow therefore proceeds to S240. A region of interest is determined at S240 based on the difference determined at S235. The significance of the region of interest will be made clear by the description below. As will be seen, the size and location of the region of interest may be determined based on the speed of device insertion, the size of the interventional device, the direction of insertion, etc. In this regard, FIG. 5 indicates region of interest 420 within image 400. Region 420 surrounds the voxels depicting device 410, and is intended to surround immediately-subsequent locations of device 410.

Figure 6:
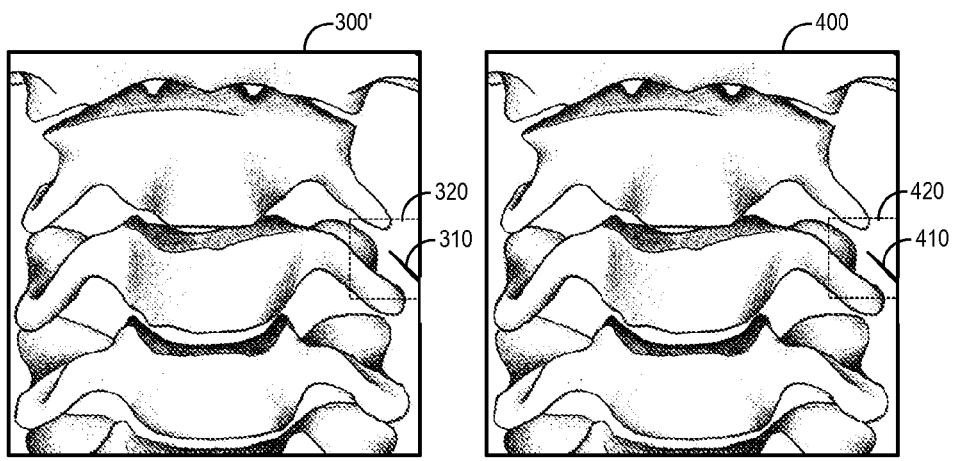
FIG. 6 comprises views of a three-dimensional image of a portion of a body with substituted voxels and a later-obtained three-dimensional image of the portion of the body.

Next, at S245, voxels in the region of interest of the first three-dimensional image are replaced with voxels of the region of interest of the second three-dimensional image, resulting in generation of an updated three-dimensional image. FIG. 6 illustrates updated image 300' according to some embodiments. Region 320 is depicted to show its correspondence to region 420 of image 400. As also shown, the original voxels of region 320 have been replaced with the voxels of region 420.

Figure 7:
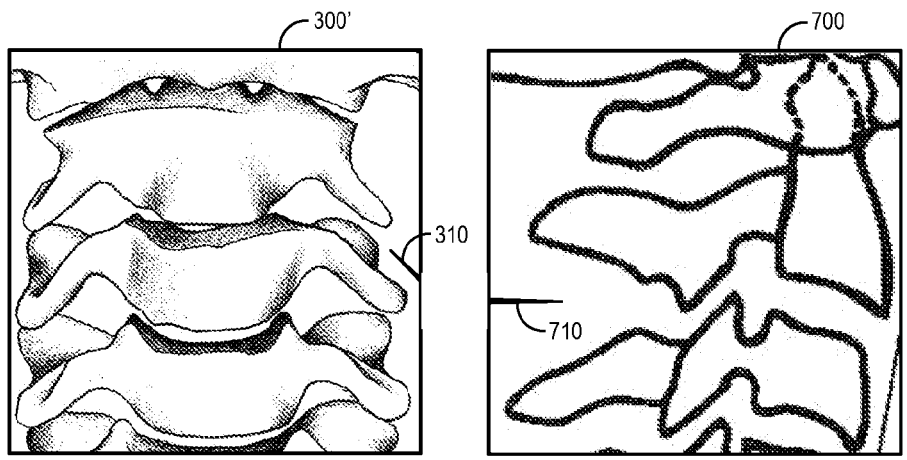
FIG. 7 comprises views of a three-dimensional image of a portion of a body with substituted voxels and a corresponding two-dimensional image of the portion of the body.

Updated image 300' is displayed to the operator at S250, as shown in FIG. 7. Continuing with the example of FIG. 3, updated image 300' and corresponding two-dimensional image 700 are simultaneously displayed. Image 700, which includes pixels 710 representing the interventional device, may be one of the two-dimensional images used to generate three-dimensional image 400.

It is then determined at S255 whether the region of interest should be updated. It will initially be assumed that the determination is negative, causing flow to continue to S260. S260 comprises a determination of whether the three-dimensional image displayed to the operator should be updated. This determination may be based on whether a predetermined period has elapsed since a last update. The predetermined period may be based on a speed of insertion, may be adaptive based on input from the operator, etc.

Once the period elapses, a next at least two two-dimensional images are acquired at S265. The at least two two-dimensional images may be acquired at S265 in any manner, and the number of images acquired at S265 may be the same or different than the number acquired at S225 or S205. A next three-dimensional image of the region of interest is generated at S270 based on the two-dimensional images acquired at S265.

Generation of the three-dimensional image at S270 may utilize less processing power than generation of the first three-dimensional image at S210, because only a suitable three-dimensional image of the region of interest is required. Accordingly, the three-dimensional reconstruction algorithm used at S270 may be tuned, using known techniques, so that image regions other than the region of interest are generated at a lower degree of resolution than that of the region of interest, or not generated at all.

Figure 8:
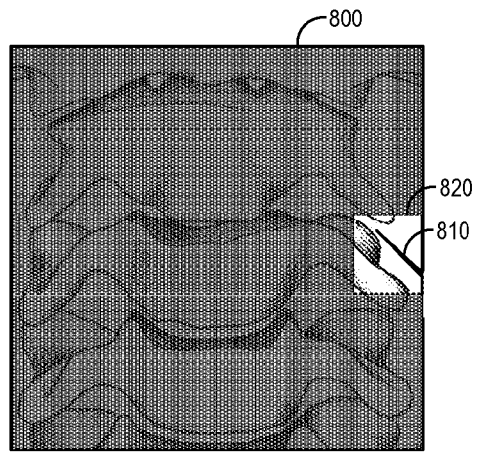
FIG. 8 comprises a view of a three-dimensional image of a portion of a body generated with respect to a predetermined region of interest.

FIG. 8 depicts three-dimensional image 800 generated at S270 according to some embodiments. Regions other than region 820 exhibit a lower resolution. Within region 820, needle 810 is shown as inserted further within the patient than in earlier figures. However, due to the size and location of region of interest 820, region 820 still includes all the voxels which represent needle 810.

Figure 9:
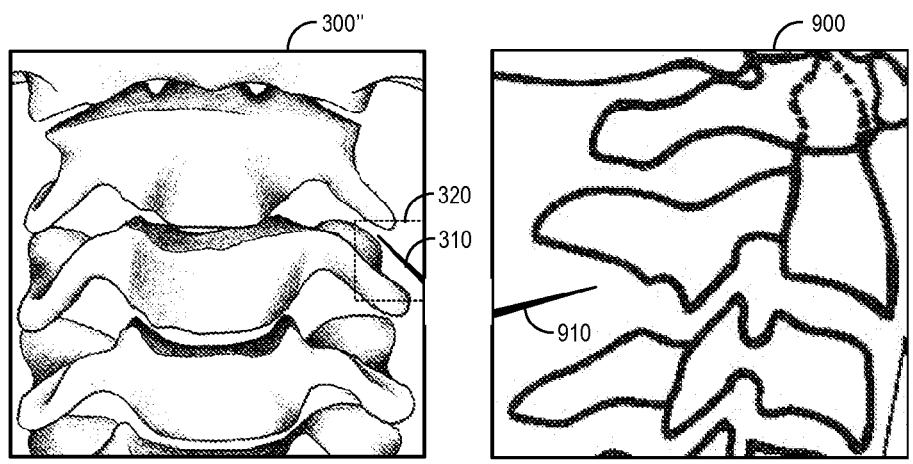
FIG. 9 comprises views of a three-dimensional image of a portion of a body with substituted voxels and a corresponding two-dimensional image of the portion of the body.

Next, at S275, voxels in the region of interest of the first three-dimensional image are replaced with voxels of the region of interest of the next three-dimensional image of S270, resulting in generation of yet another updated three-dimensional image. Flow returns to S250 to display the updated image to the operator, as shown in FIG. 9. As shown, the original voxels of region 320 have been replaced with the voxels of region 820 of image 800. Also shown is simultaneously-displayed corresponding two-dimensional image 900. Image 900 includes pixels 910 representing the interventional device, and may be one of the two-dimensional images used to generate three-dimensional image 800.

Flow continues as described above to acquire a next at least two two-dimensional images at S265 and to generate a corresponding three-dimensional image based thereon at S270. Again, generation of the three-dimensional image at S270 may utilize less processing power than generation of the first three-dimensional image at S210, because only a suitable three-dimensional image of the region of interest is required.

Figure 10:
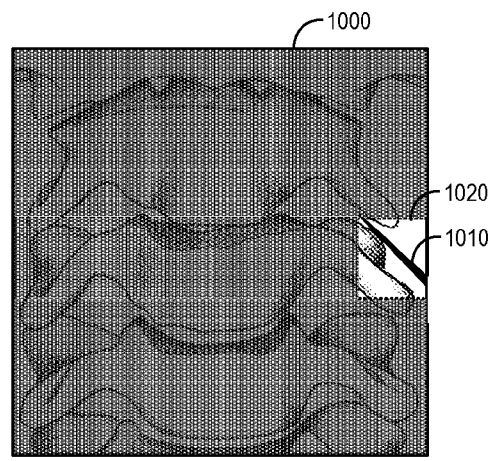
FIG. 10 comprises a view of a three-dimensional image of a portion of a body generated with respect to a predetermined region of interest.
Figure 11:
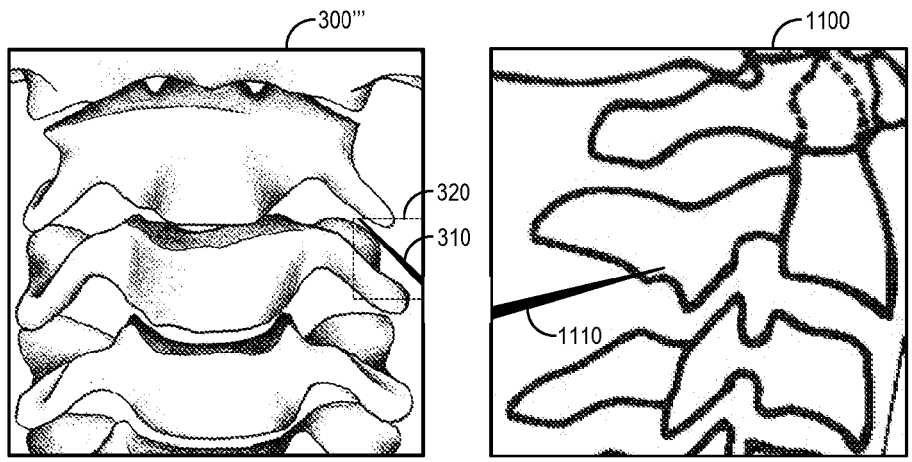
FIG. 11 comprises views of a three-dimensional image of a portion of a body with substituted voxels and a corresponding two-dimensional image of the portion of the body.

FIG. 10 depicts three-dimensional image 1000 generated at S270 according to some embodiments. Within region 1020, needle 1010 is shown as inserted further within the patient than in earlier figures. FIG. 11 depicts replacement of the original voxels of region 320 with the voxels of region 1020 of image 1000 to generate updated image 300′″. Also-displayed two-dimensional image 1100 includes pixels 1110 representing the interventional device, and may be one of the two-dimensional images used to generate three-dimensional image 1000.

Flow therefore cycles from S250 through S275 to periodically update the displayed three-dimensional image during the interventional procedure. Since only the three-dimensional region of interest is updated, some embodiments provide three-dimensional monitoring of an interventional procedure while using less processing power than prior systems.

It will now be assumed that, during the aforementioned cycling, it is determined at S255 to update the region of interest. The determination may be based on a command input by the operator, on an elapsed time period, on a determination that voxels near a boundary of the region have changed, or on any other factor. Flow returns to S225 after this determination.

As described above, at least two two-dimensional images are acquired at S225 and a three-dimensional image is generated based thereon at S230. At S235, it is determined whether this three-dimensional image differs sufficiently from the first three-dimensional image generated at S210.

Figure 12:
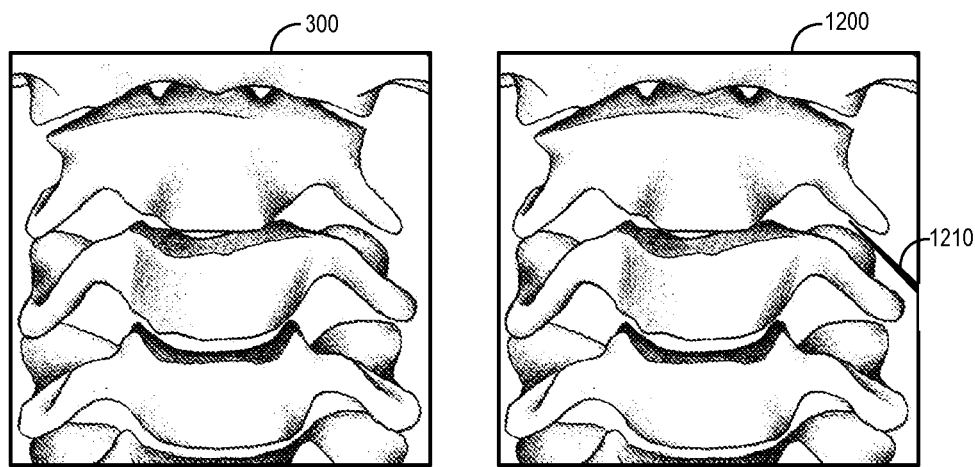
FIG. 12 comprises views of a three-dimensional image of a portion of a body and a later-obtained three-dimensional image of the portion of the body.

FIG. 12 illustrates first three-dimensional image 300 and new three-dimensional image 1200. As mentioned above, both of these images are most likely not simultaneously presented to the operator. Three-dimensional image 1200 depicts needle 1210, and it is assumed that the difference between image 300 and image 1200 results in an affirmative determination at S235.

Figure 13:
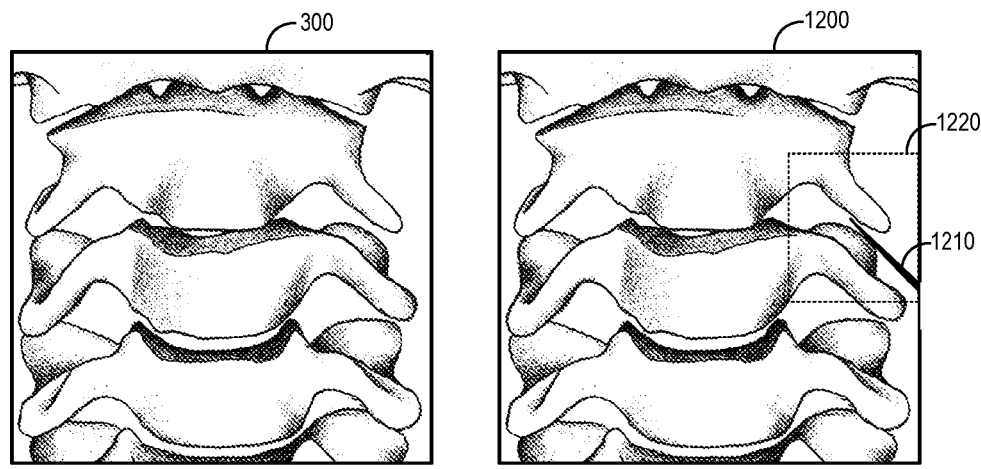
FIG. 13 comprises views of a three-dimensional image of a portion of a body and a later-obtained three-dimensional image of the portion of the body illustrating detection of a changed region.
Figure 14:
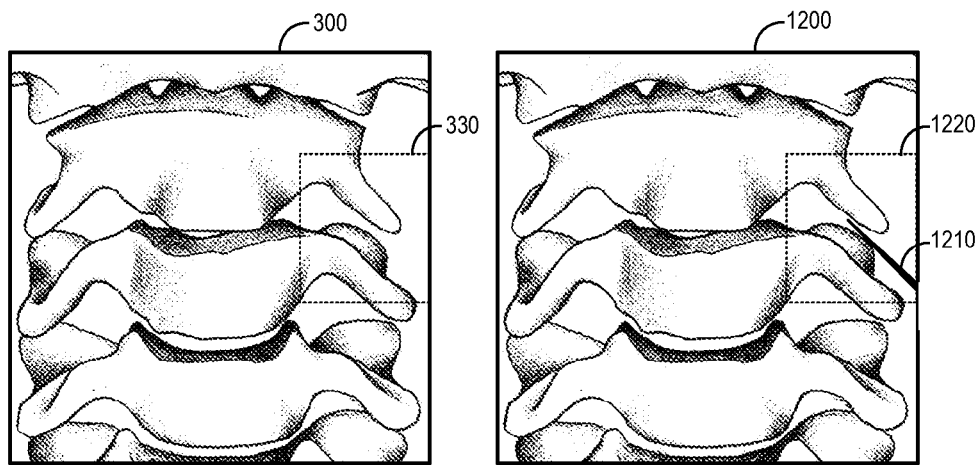
FIG. 14 comprises views of a three-dimensional image of a portion of a body illustrating a region of interest and a later-obtained three-dimensional image of the portion of the body illustrating a changed region.
Figure 15:
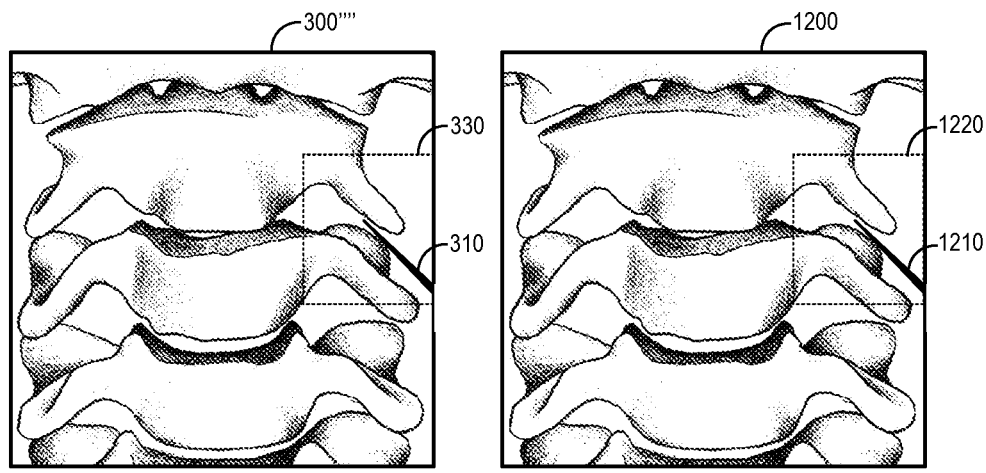
FIG. 15 comprises views of a three-dimensional image of a portion of a body with substituted voxels and a later-obtained three-dimensional image of the portion of the body.

A region of interest is determined at S240 based on the difference determined at S235. FIG. 13 indicates region of interest 1220 determined according to the present example. Voxels in the region of interest of the first three-dimensional image are replaced at S245 with voxels of the new region of interest of the new three-dimensional image, resulting in generation of an updated three-dimensional image. FIG. 14 shows region 330 of image 300 corresponding to newly-determined region 1220, and FIG. 15 shows replacement of the original voxels of region 330 have been replaced with the voxels of region 1220 of image 1200.

Figure 16:
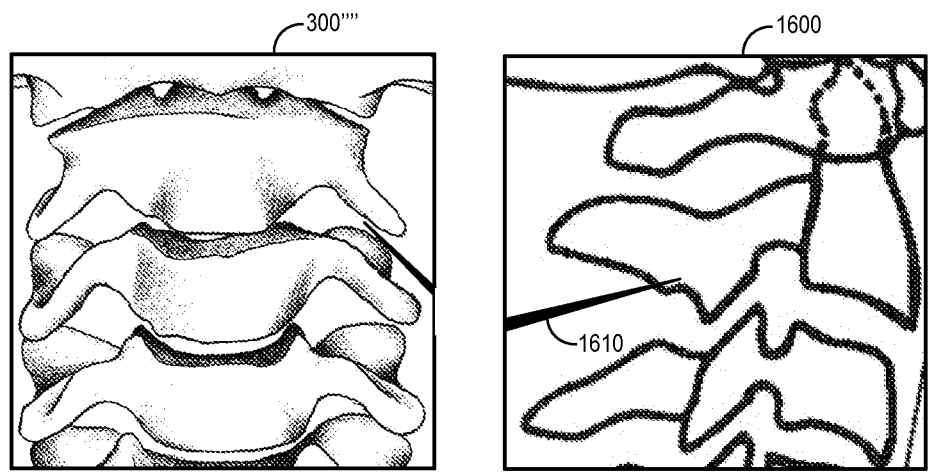
FIG. 16 comprises views of a three-dimensional image of a portion of a body with substituted voxels and a corresponding two-dimensional image of the portion of the body.

Updated image 300″″ is displayed to the operator at S250, as shown in FIG. 16. Two-dimensional image 1600 is also displayed, including includes pixels 1610 representing the interventional device. Image 1600 may be one of the two-dimensional images used to generate three-dimensional image 1200.

Flow may continue as described above to display updated three-dimensional images until the operator decides to terminate the process.

Figure 17:
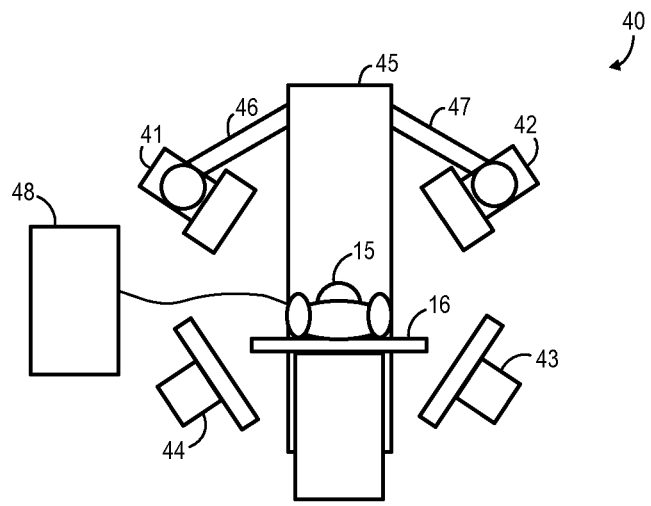
FIG. 17 illustrates a system according to some embodiments.
Figure 18:
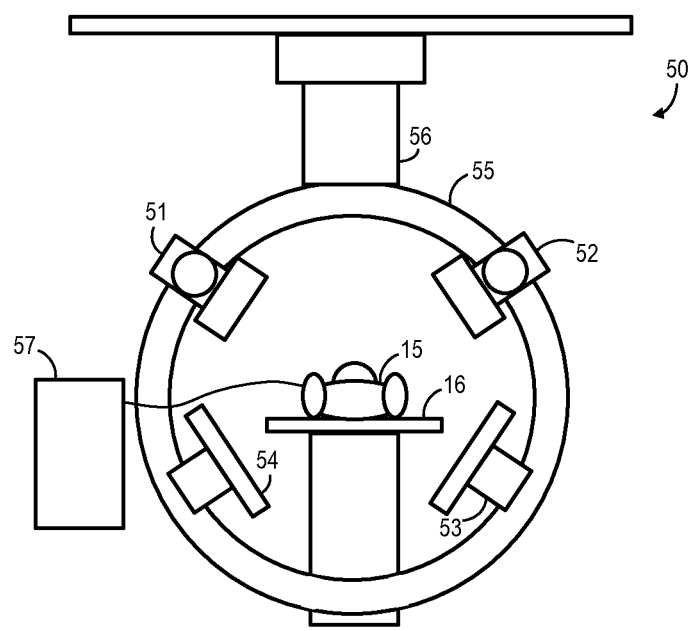
FIG. 18 illustrates a system according to some embodiments.

FIGS. 17 and 18 illustrate other systems which may implement the processes described above. Embodiments are not limited to the systems depicted herein. System 40 of FIG. 17 includes two radiation sources 41, 42 and corresponding detectors 43, 44. Radiation sources 41, 42 are attached to gantry 45 via supports 46, 47, respectively. System 40 may operate to acquire two two-dimensional images simultaneously. According to some implementations, the positions of sources 41, 42 and detectors 43, 44 may be changed to change the projection angle from which the images are acquired.

System 50 of FIG. 18 also includes two radiation sources 51, 52 and associated radiation detectors 53, 54. Sources 51, 52 and detectors 53, 54 are mounted to gantry 55, which is configured to translate with respect to support 56. Translation of gantry 55 facilitates acquisition of two simultaneous images from various projection angles.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A system comprising:
an imaging system configured to:
acquire a first at least two two-dimensional images of a body; and
acquire a second at least two two-dimensional images of the body;
an image processor configured to:
generate a first three-dimensional image based on the first at least two two-dimensional images;
generate a second three-dimensional image based on the second at least two two-dimensional images;
determine a difference between the first three-dimensional image and the second three-dimensional image;
determine a region of interest based on the difference; and
replace first voxels of the region of interest of the first three-dimensional image with second voxels of the region of interest of the second three-dimensional image to generate a first updated three-dimensional image; and
a display configured to display the first updated three-dimensional image.

2. A system according to claim 1,
wherein the first voxels of the region of interest of the first three-dimensional image do not depict an interventional medical device and the second voxels of the region of interest of the second three-dimensional image depict the interventional medical device.

3. A system according to claim 1,
the imaging system further configured to:
acquire a third at least two two-dimensional images of the body;
the image processor further configured to:
generate a third three-dimensional image based on the third at least two two-dimensional images; and
replace voxels of the region of interest of the first updated three-dimensional image with third voxels of the region of interest of the third three-dimensional image to generate a second updated three-dimensional image; and
the display further configured to:
display the second updated three-dimensional image.

4. A system according to claim 3,
wherein the first voxels of the region of interest of the first three-dimensional image do not depict an interventional medical device, the second voxels of the region of interest of the second three-dimensional image depict the interventional medical device, and the third voxels of the region of interest of the third three-dimensional image depict the interventional medical device.

5. A system according to claim 3,
the imaging system further configured to:
acquire a fourth at least two two-dimensional images of the body;
the image processor further configured to:
generate a fourth three-dimensional image based on the fourth at least two two-dimensional images;
determine a second difference between the first three-dimensional image and the fourth three-dimensional image;
determine a second region of interest based on the second difference; and
replace voxels of the second region of interest of the first three-dimensional image with voxels of the second region of interest of the fourth three-dimensional image to generate a third updated three-dimensional image; and
the display further configured to:
display the third updated three-dimensional image.

6. A system according to claim 1,
the imaging system further configured to:
acquire a third at least two two-dimensional images of the body;
the image processor further configured to:
generate a third three-dimensional image based on the third at least two two-dimensional images;
determine a second difference between the first three-dimensional image and the third three-dimensional image;
determine a second region of interest based on the second difference; and
replace voxels of the second region of interest of the first updated three-dimensional image with voxels of the second region of interest of the third three-dimensional image to generate a second updated three-dimensional image; and
the display further configured to:
display the second updated three-dimensional image.

7. A method comprising:
acquiring a first at least two two-dimensional images of a body;
generating a first three-dimensional image based on the first at least two two-dimensional images;
acquiring a second at least two two-dimensional images of the body;
generating a second three-dimensional image based on the second at least two two-dimensional images;
determining a difference between the first three-dimensional image and the second three-dimensional image;
determining a region of interest based on the difference;
replacing first voxels of the region of interest of the first three-dimensional image with second voxels of the region of interest of the second three-dimensional image to generate a first updated three-dimensional image; and
displaying the first updated three-dimensional image.

8. A method according to claim 7,
wherein the first voxels of the region of interest of the first three-dimensional image do not depict an interventional medical device and the second voxels of the region of interest of the second three-dimensional image depict the interventional medical device.

9. A method according to claim 7, further comprising:
acquiring a third at least two two-dimensional images of the body;
generating a third three-dimensional image based on the third at least two two-dimensional images;
replacing voxels of the region of interest of the first updated three-dimensional image with third voxels of the region of interest of the third three-dimensional image to generate a second updated three-dimensional image; and
displaying the second updated three-dimensional image.

10. A method according to claim 9,
wherein the first voxels of the region of interest of the first three-dimensional image do not depict an interventional medical device, the second voxels of the region of interest of the second three-dimensional image depict the interventional medical device, and the third voxels of the region of interest of the third three-dimensional image depict the interventional medical device.

11. A method according to claim 9, further comprising:
acquiring a fourth at least two two-dimensional images of the body;
generating a fourth three-dimensional image based on the fourth at least two two-dimensional images;
determining a second difference between the first three-dimensional image and the fourth three-dimensional image;
determining a second region of interest based on the second difference;
replacing voxels of the second region of interest of the first three-dimensional image with voxels of the second region of interest of the fourth three-dimensional image to generate a third updated three-dimensional image; and
displaying the third updated three-dimensional image.

12. A method according to claim 7, further comprising:
acquiring a third at least two two-dimensional images of the body;
generating a third three-dimensional image based on the third at least two two-dimensional images;
determining a second difference between the first three-dimensional image and the third three-dimensional image;
determining a second region of interest based on the second difference;
replacing voxels of the second region of interest of the first updated three-dimensional image with voxels of the second region of interest of the third three-dimensional image to generate a second updated three-dimensional image; and
displaying the second updated three-dimensional image.

13. A non-transitory computer-readable medium storing processor-executable program code, the program code executable to cause a processor to:
acquire a first at least two two-dimensional images of a body;
generate a first three-dimensional image based on the first at least two two-dimensional images;
acquire a second at least two two-dimensional images of the body;
generate a second three-dimensional image based on the second at least two two-dimensional images;
determine a difference between the first three-dimensional image and the second three-dimensional image;
determine a region of interest based on the difference;
replace first voxels of the region of interest of the first three-dimensional image with second voxels of the region of interest of the second three-dimensional image to generate a first updated three-dimensional image; and
display the first updated three-dimensional image.

14. A medium according to claim 13,
wherein the first voxels of the region of interest of the first three-dimensional image do not depict an interventional medical device and the second voxels of the region of interest of the second three-dimensional image depict the interventional medical device.

15. A medium according to claim 13, the program code further executable to cause a processor to:
acquire a third at least two two-dimensional images of the body;
generate a third three-dimensional image based on the third at least two two-dimensional images;
replace voxels of the region of interest of the first updated three-dimensional image with third voxels of the region of interest of the third three-dimensional image to generate a second updated three-dimensional image; and
display the second updated three-dimensional image.

16. A medium according to claim 15,
wherein the first voxels of the region of interest of the first three-dimensional image do not depict an interventional medical device, the second voxels of the region of interest of the second three-dimensional image depict the interventional medical device, and the third voxels of the region of interest of the third three-dimensional image depict the interventional medical device.

17. A medium according to claim 15, the program code further executable to cause a processor to:
acquire a fourth at least two two-dimensional images of the body;
generate a fourth three-dimensional image based on the fourth at least two two-dimensional images;
determine a second difference between the first three-dimensional image and the fourth three-dimensional image;
determine a second region of interest based on the second difference;
replace voxels of the second region of interest of the first three-dimensional image with voxels of the second region of interest of the fourth three-dimensional image to generate a third updated three-dimensional image; and
display the third updated three-dimensional image.

18. A medium according to claim 13, the program code further executable to cause a processor to:
acquire a third at least two two-dimensional images of the body;
generate a third three-dimensional image based on the third at least two two-dimensional images;
determine a second difference between the first three-dimensional image and the third three-dimensional image;
determine a second region of interest based on the second difference;
replace voxels of the second region of interest of the first updated three-dimensional image with voxels of the second region of interest of the third three-dimensional image to generate a second updated three-dimensional image; and
display the second updated three-dimensional image.

* * * * *